(12) United States Patent
Li et al.

(10) Patent No.: US 7,390,669 B2
(45) Date of Patent: Jun. 24, 2008

(54) SIMULTANEOUS AND RAPID DETERMINATION OF MULTIPLE COMPONENT CONCENTRATIONS IN A KRAFT LIQUOR PROCESS STREAM

(75) Inventors: Jian Li, Marietta, GA (US); Xin Sheng Chai, Atlanta, GA (US); Junyoung Zhu, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 715 days.

(21) Appl. No.: 10/999,912

(22) Filed: Nov. 30, 2004

(65) Prior Publication Data

US 2005/0139337 A1 Jun. 30, 2005

Related U.S. Application Data

(63) Continuation of application No. 09/513,207, filed on Feb. 24, 2000, now abandoned.

(51) Int. Cl.
G01N 21/01 (2006.01)
G01N 33/34 (2006.01)
D21C 7/12 (2006.01)

(52) U.S. Cl. ............................ 436/165; 162/49; 162/50; 162/61; 162/62; 162/263; 250/373; 422/62; 422/68.1; 422/82.09; 422/82.11; 436/100; 436/102; 436/121; 436/131; 436/133; 436/182

(58) Field of Classification Search ............. 162/49–50, 162/61–62, 263; 250/372–373; 356/36, 356/246; 422/62, 68.1, 82.09, 82.11; 436/53, 436/73, 79, 93–94, 10, 102, 119, 121, 127–129, 436/131, 133, 164–165, 182–183
See application file for complete search history.

(56) References Cited

U.S. PATENT DOCUMENTS 4,175,864 A * 11/1979 Gilby ........................ 356/326
4,611,143 A * 9/1986 Shimazu et al. ............. 313/111
4,718,979 A * 1/1988 Tikka et al. ................... 162/49
4,749,656 A * 6/1988 Ellerbe ........................ 436/83
4,829,186 A * 5/1989 McLachlan et al. ......... 250/373

(Continued)

FOREIGN PATENT DOCUMENTS

| DE | 2837769 | * | 3/1980 |
| WO | 96/14569 | * | 5/1996 |
| WO | 97/10501 | * | 3/1997 |

OTHER PUBLICATIONS

Ley, H. et al, Z. Physik. Chem. B 1930, 4, 240-246.*

(Continued)

*Primary Examiner*—Arlen Soderquist
(74) *Attorney, Agent, or Firm*—Ryan A. Schneider, Esq.; Troutman Sanders LLP (57) ABSTRACT

The present invention is a rapid method of determining the concentration of the major components in a chemical stream. The present invention is also a simple, low cost, device of determining the in-situ concentration of the major components in a chemical stream. In particular, the present invention provides a useful method for simultaneously determining the concentrations of sodium hydroxide, sodium sulfide and sodium carbonate in aqueous kraft pulping liquors through use of an attenuated total reflectance (ATR) tunnel flow cell or optical probe capable of producing a ultraviolet absorbency spectrum over a wavelength of 190 to 300 nm. In addition, the present invention eliminates the need for manual sampling and dilution previously required to generate analyzable samples. The inventive method can be used in Kraft pulping operations to control white liquor causticizing efficiency, sulfate reduction efficiency in green liquor, oxidation efficiency for oxidized white liquor and the active and effective alkali charge to kraft pulping operations.

28 Claims, 6 Drawing Sheets

U.S. PATENT DOCUMENTS

| | | | | |
|---|---|---|---|---|
| 4,966,458 | A | * | 10/1990 | Burns et al. .................. 356/328 |
| 4,988,195 | A | * | 1/1991 | Doyle .......................... 356/244 |
| 5,054,920 | A | * | 10/1991 | Doyle .......................... 356/246 |
| 5,117,150 | A | * | 5/1992 | Schwarz et al. ............. 313/112 |
| 5,190,882 | A | * | 3/1993 | Schulz et al. ................ 436/139 |
| 5,242,602 | A | * | 9/1993 | Richardson et al. .......... 210/745 |
| 5,282,931 | A | | 2/1994 | LeClere et al. |
| 5,311,274 | A | * | 5/1994 | Cole, Jr. ....................... 356/133 |
| 5,364,502 | A | | 11/1994 | LeClere et al. |
| 5,378,320 | A | | 1/1995 | Leclere et al. |
| 5,582,684 | A | * | 12/1996 | Holmqvist et al. ............. 162/49 |
| 5,610,405 | A | * | 3/1997 | Inushima et al. ............. 250/372 |
| 5,616,214 | A | | 4/1997 | Leclere et al. |
| 5,641,966 | A | * | 6/1997 | Karlberg et al. .............. 250/373 |
| 5,801,820 | A | * | 9/1998 | Bysouth et al. ................ 356/36 |
| 5,991,029 | A | * | 11/1999 | Doyle .......................... 356/451 |
| 6,003,362 | A | * | 12/1999 | Dieckmann et al. ......... 73/19.12 |
| 6,023,065 | A | * | 2/2000 | Garver, Jr. ................... 250/372 |

OTHER PUBLICATIONS

Kessler, A., Czech. J. Phys. 1969, 19, 689-696.*
Nilsson-Idner, K. et al, Sv. Papperstidn. 1974, 77, 60-62.*
Armstrong, F. A. J., ASTM Spec. Tech. Publ. 1975, 573, 14-19.*
Uronen, P. et al, Environ. Syst. Plann., Des. Control, Proc. IFAC Symp. 1978, 1, 55-60.*
Schlemmer, H. et al, Fresenius' Z. Anal. Chem. 1987, 329, 435-439.*
Schlemmer, H. et al, GIT Fachz. Lab. 1990, 34, 257-258 and 261-263.*
Salomon, D. R. et al, Process Control Qual. 1992, 3, 219-227.*
Wang, I. et al, Fenxi Huaxue 1993, 21, 425-427.*
Mel'nikova, N. B. et al, Zh. Prikl. Khim. 1993, 66, 2080-2085.*
Rinke, G. et al, Tech. Mess. 1994, 61, 204-207.*
Danielsson, L.-G. et al, Process Control Qual. 1994, 6, 149-157.*
Zhu, D. et al, Fenxi Huahua 1995, 23, 858-861.*
Kiriyama, T., Kagoshima Daigaku Kyoikugakubu Kenkyu Kiyo, Shizen Kagaku Hen 1996, 48, 65-70.*
Masselter, S. W. et al, J. High Resolut. Chromatogr. 1996, 19, 131-136.*
Chai, X.-S. et al, Process Control and Quality 1998, 11, 153-159.*
Doyle, W. M. et al, Spectroscopy 1999, 14, 46, 48, and 50-54.*
Romppainen, P. et al, Process Control Qual. 1999, 11, 255-263.*
Xin-Sheng Chai, "Process Analytical Chemistry Applied to Liquors in the Pulping Industry", Ph.D. Dissertation, 1996, Swedish Centre for Process Analytical.Chemistry, The Royal Institute of Technology, S-100 44, Stockholm, Sweden, ISBN 91-7170-653-4.
"Axiom Paper Breaks New Ground", no author given, p. 1, Axiom Bulletin, Fall 1998, company newsletter published by Axiom Analytical Incorporated, Irvine, California, 92614.

* cited by examiner

SIMULTANEOUS AND RAPID DETERMINATION OF MULTIPLE COMPONENT CONCENTRATIONS IN A KRAFT LIQUOR PROCESS STREAM

This application is a continuation of application Ser. No. 09/513,207, filed 24 Feb. 2000, now abandoned, which is herein incorporated by reference in its entirety.

STATEMENT OF GOVERNMENT INTEREST

This invention was made with support under Contract No. DE-FC07-96ID 13428 awarded by the United States Department of Energy. The United States Government has certain rights in this invention.

FIELD OF THE INVENTION

The present invention relates to a means for rapidly determining the concentration of major components of a chemical processing stream. More particularly, the present invention relates to a method for determining the concentration of major components of a processing stream in real time, through the use of attenuated total reflectance and ultraviolet spectroscopy to measure absorbency. The present invention also relates to the determination of the concentration of major components in an aqueous liquor used in the manufacture of cellulosic pulps. Still more particularly, the present invention relates to a method for simultaneously determining the concentrations of sodium sulfide, sodium carbonate and sodium hydroxide in kraft liquors.

BACKGROUND OF THE INVENTION

Conventional ultraviolet (UV) spectroscopy represents one of the least expensive methods for measuring component concentrations of a chemical process stream. However, conventional UV technology requires significant dilution of the process stream and many chemical components such as NaOH and $Na_2CO_3$ do not absorb ultraviolet radiation in the wavelength range currently measurable by conventional UV spectroscopy.

To overcome the dilution problems associated with utilizing conventional UV spectroscopy equipment, those skilled in the art have employed attenuated total reflectance (ATR) probes for analyzing process streams. Such methods are disclosed in Chai et. al., Spectrophotometric In-Line Monitoring of the Electrochemical Production of Polysulfides Using an ATR-Probe, Process Control and Quality, Vol. 11, No. 2, p. 153 (1998); Schlemmer et. al., ATR technique for UV/Vis Analytical Measurements, Fresenious Z Analytical Chemistry, Vol. 329, pp. 435-439 (1987); and Chai, Process Analytical Chemistry Applied to Liquors in the Pulping Industry, Swedish Centre for Process Analytical Chemistry, The Royal Institute of Technology, S-100 44, Stockholm, Sweden, ISBN 91-7179-653-4. However, ATR probes employed by the prior art are incapable of providing useful absorbency data below 210 nm which limits their application to process streams containing chemical components which absorb ultraviolet light above 210 nm.

In particular, this significant limitation prevents those skilled in the art from simultaneously determining the three major components found in paper mill kraft liquor streams. Two key components of kraft liquor streams, NaOH and $Na_2CO_3$, could not heretofore be individually detected because NaOH and $Na_2CO_3$ do not absorb ultraviolet light above 210 nm. Therefore, NaOH and $Na_2CO_3$ are commonly considered a single component referred to in the prior art as non-absorbing components or part of the total non-absorbing salt concentration. Because NaOH and $Na_2CO_3$ are non-absorbing above a wavelength of 210 nm the component concentrations of NaOH and $Na_2CO_3$ cannot be analyzed separately and determined individually.

Accurate determination of NaOH and $Na_2CO_3$ concentrations is critical to the operation of many kraft mill processes. In kraft pulping, lignocellulosic material, e.g., wood chips, is treated with an aqueous liquor containing active pulping chemicals, referred to as a white liquor. The white liquor typically contains sodium hydroxide and sodium sulfide, the two active cooking chemicals.

The fibers that make up the wood chips are separated from one another when the lignin that binds them together is dissolved in the white liquor at an elevated temperature. Once the fibers have been separated, the spent cooking liquor is collected. This spent pulping liquor is referred to as black liquor. The concentrated black liquor is burned in a chemical recovery furnace where the sulfur compounds are reduced to sodium sulfide. The inorganic ash recovered from this process is then dissolved in water producing what is referred to as green liquor. The green liquor contains primarily sodium sulfide and sodium carbonate. The green liquor can be converted into white liquor, by contacting the green liquor with calcium hydroxide in water. This process converts sodium carbonate ($Na_2CO_3$) into sodium hydroxide (NaOH) and is referred to as recausticizing.

The rate and selectivity of delignification in the pulping process is strongly affected by the quality of the white liquor. The quality of the white liquor is defined by the concentrations of the sodium hydroxide and the sodium sulfide ($Na_2S$). High quality white liquor has high concentrations of NaOH and $Na_2S$, and low concentrations of $Na_2CO_3$ and sodium sulfate ($Na_2SO_4$). To control the pulping process, it is necessary to monitor and adjust the relative concentration of the major components. This control can only be achieved if accurate measurements can be taken in-situ, thus allowing the process operator to make timely adjustments to the concentrations.

Known sensors for white liquor analysis are based upon conductivity, Fourier-Transform infrared FTIR, near infrared (NIR) or conventional UV spectroscopy. However, sensors based upon conductivity, FTIR and conventional UV spectroscopy can only provide a single component measurement. For example, FTIR and conductivity only detect the EA concentration. Likewise, conventional UV can only provide sulfide concentration.

Prior art methods based upon NIR like that disclosed in U.S. Pat. No. 5,616,214 may provide a means for simultaneously measuring the component concentrations of a kraft liquor stream. However, the NIR equipment necessary to conduct the analysis disclosed in the '214 patent is prohibitively expensive.

While conventional UV spectroscopy equipment is considerably cheaper than NIR, it too has certain disadvantages. The primary disadvantage of conventional UV spectroscopy is that it requires very high dilution rates, on the order of 10,000, before the process liquor can be analyzed. Also, since dissolved oxygen can react with sulfide and therefore greatly affect the accuracy of the measurements, it has heretofore been necessary to deoxygenate the samples prior to evaluation with conventional UV spectroscopy.

Accordingly, of the three primary components of a kraft liquor stream whose concentrations are critical to kraft operations (NaOH, $Na_2CO_3$ and $Na_2S$), only the concentration of $Na_2S$ could be determined using prior art techniques. While the combined concentration of the non-absorbing salts, NaOH and $Na_2CO_3$, can individually be determined using the prior art methods, this total non-absorbing salt concentration cannot be used to effectively control kraft mill operations.

Thus, there exists a need for a rugged, inexpensive, simple analysis method and apparatus that can be used directly in the processing line, or in an associated flow cell that will provide the individual concentrations of all the major components within a kraft liquor stream without dilution of the liquor sample.

The inventive system provides individual concentration information for NaOH, $NaCO_3$ and $Na_2S$ in real time, without dilution of the liquor sample. Thus, the present invention allows for immediate concentration adjustments resulting in improved kraft mill operation. The analyzer of the present invention can be installed directly in a pulping liquor stream as a probe or can be incorporated as part of a sample system as a flow cell. The analyzer of the present invention costs significantly less than competing infrared technologies and is simple to operate.

Further advantages of the invention will be set forth in part in the description which follows and in part will be apparent from the description or may be learned by practice of the invention. The advantages of the invention may be realized and attained by means of the instrumentalities and combinations particularly pointed out in the appended claims.

SUMMARY OF THE INVENTION

To achieve the foregoing advantages and in accordance with the purpose of the invention, as embodied and broadly described herein, there is disclosed:

A method for simultaneously determining multiple chemical concentrations of a liquid stream comprising:

(a) subjecting at least a segment of the stream to ultraviolet light wherein the light penetrates a short distance into the segment and the effective path length of the light is a function of the refractive index of the segment;

(b) generating an ultraviolet absorption spectrum from said ultraviolet penetration of the segment over a wavelength from 190 to 300 nm; and (c) analyzing the ultraviolet absorption spectrum by a regression method to determine the component concentrations of the liquid stream.

There is further disclosed:

A method for simultaneously determining the sodium hydroxide, sodium sulfide and sodium carbonate concentrations of a kraft liquor stream comprising:

(a) generating an ATR-UV absorbency spectrum of the liquor over a wavelength from 190 to 300 nm;

(b) analyzing the ultraviolet absorption spectrum by a regression method to determine the component concentrations of the liquor.

There is still further disclosed:

A system for determining chemical concentrations of a liquid stream comprising:

(a) an ultraviolet spectrometer, (b) a device capable of providing ultraviolet absorption data between 190 and 300 nm, and (c) a multivariate or linear calibration program for analyzing the ultraviolet absorption data.

There is still further disclosed:

A system for determining chemical concentrations of NaOH and $Na_2CO_3$ in a kraft liquor stream comprising:

an ultraviolet spectrometer, an attenuated total reflectance device capable of providing ultraviolet absorption data between 190 and 300 nm wherein the attenuated total reflectance device transmits the ultraviolet absorption data to the ultraviolet spectrometer by fiber optic cable, a multivariate or linear calibration program for analyzing the ultraviolet absorption data.

The accompanying drawings are included to provide a further understanding of the invention and are incorporated in and constitute a part of the specification. The drawings illustrate embodiments of the invention, and together with the description, serve to explain the principles of the invention.

DETAILED DESCRIPTION

The present invention is directed to on-line and in-line systems and a method for simultaneously determining component concentrations of chemicals absorbing ultraviolet radiation in the wavelength range of 190-300 nm including effective alkali, carbonate and sulfide concentrations in kraft liquors used for kraft pulp manufacturing processes. The device used in this method is rugged; inexpensive, and easy to install and operate. The device provides rapid and simultaneous output of several component concentrations from a single sampling and analysis of the liquor stream, including concentrations of NaOH and $Na_2CO_3$ which absorb radiation in the wavelength range from 190-210 nm. The method may be practiced using a system configured for in-line or on-line sampling.

Figure 1:
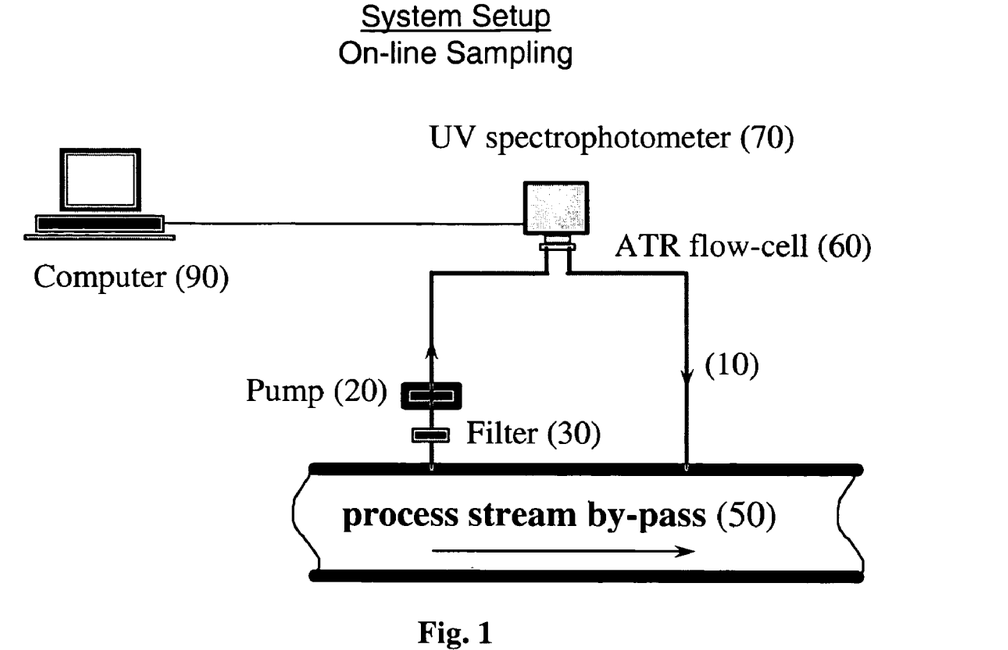
FIG. 1 illustrates an embodiment of the present invention where the sensor is used in conjunction with a flow cell.

FIG. 1 illustrates one preferred embodiment of the inventive system as configured for on-line measurement. The system includes a sample line (10) and pump (20) for periodically or continuously withdrawing a chemical stream or a segment of it from a tank, reactor or transport line (50). In one more preferred embodiment, the sample line (10) includes a filter (30) for removing solid particles. The pump draws a small sample stream or segment (40) from the target stream (50) at a preferable rate of 10-100 cc/min. The sample stream passes through the filter (30) before it enters an Attenuated Total Reflectance (ATR) Tunnel flow cell (60) which is installed in an Ultraviolet Spectrophotometer (70). Light from the spectrophotometer (70) passes through the ATR cell where some light is absorbed by the sample. The light leaves the ATR where it is returned to the spectrophotometer (70) for measurement. The spectrophotometer (70) generates a UV absorbency spectrum of the liquor sample over a predetermined range of wavelength, preferably 190-300 nm, which is recorded by a computer (90). The spectrum is then analyzed by either a multivariate or linear calibration program installed in the computer which computes the concentration of the individual chemical components.

The liquor sample may be caused to flow through the test cell using any art recognized method. Preferred methods include those that create a pressure drop thereby drawing the sample through the test cell. Such systems may include, for example, a pump or vacuum.

Figure 2:
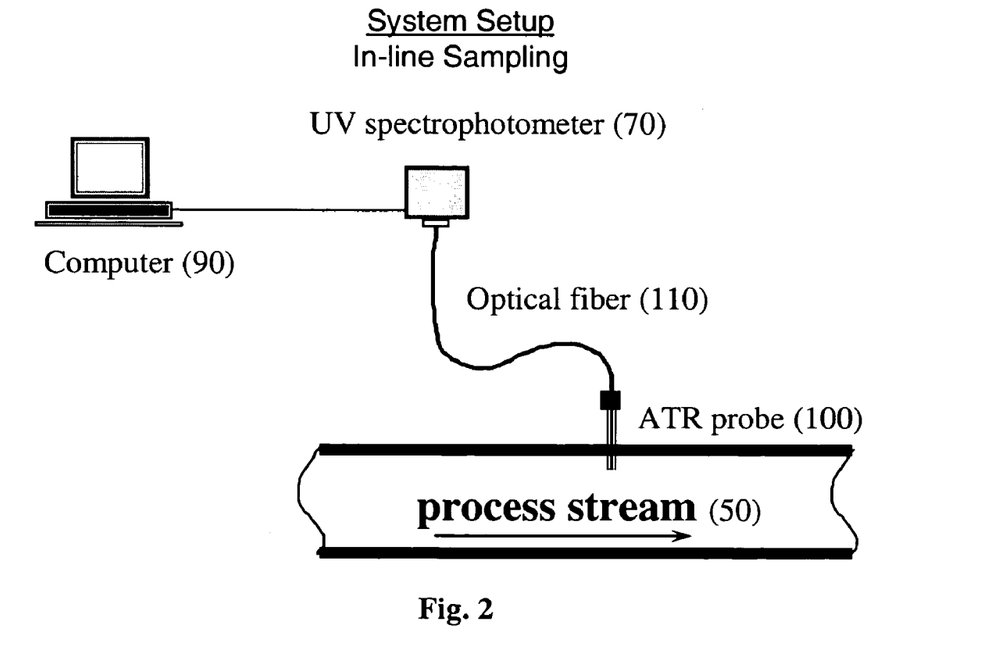
FIG. 2 illustrates an embodiment of the present invention where the sensor is placed in direct contact with the chemical process stream.

FIG. 2 illustrates a preferred embodiment of the inventive system as configured for in-line measurement. The in-line system includes an ATR optical probe (100) which is inserted directly into the targeting liquor tank, reactor, or process line (50). The ATR optical probe (100) is connected to the UV spectrophotometer (70) by optical fibers (110) which transport the light from the spectrophotometer (70) to the ATR probe (100) and the absorbency spectra from the probe to the spectrophotometer (70). The analysis of the absorbency spectra from an in-line system proceeds as described above for the on-line system.

While on-line and in-line sampling as illustrated in FIGS. 1 and 2 represent the preferred configuration for sampling a process stream and generating ATR-UV absorption data, any system which allows for contact between a process stream and an ATR probe or which generates process stream flow through an ATR tunnel flow cell is suitable for use in the claimed invention. One of ordinary skill in the art would recognize a variety of known techniques for causing the liquor to flow through the flow-cell through the use of a pressure drop. A preferred UV spectrophotometer for use in the present invention is UV-8453 produced by Hewlett-Packard; however, any art recognized UV spectrophotometer that can provide UV spectrum in the wavelength range 190-300 nm is appropriate.

The basic principles of ATR-UV technology are explained in Xin-Sheng Chai, Process Analytical Chemistry Applied To Liquors In The Pulping Industry, Doctoral Thesis, ISBN 91-7170-653-4, (1996) and Xin-Sheng Chai, L-G Danielsson, Xiaotian Yang and Marten Behm, Spectrophotometric In-Line Process Monitoring In UV-Vis Range Using An ATR-Probe, Process Control and Quality, (Vol. 11., No. 2, p.153-159 (1998), the contents of which are incorporated by reference, which disclose use of an ATR probe for measuring sulfide concentrations in kraft liquors. As explained by Chai, a significant advantage of the ATR-UV technology employed in the inventive system is the elimination of the need to dilute the stream sample as required with conventional UV spectroscopy used for industrial process analysis.

Figure 3:
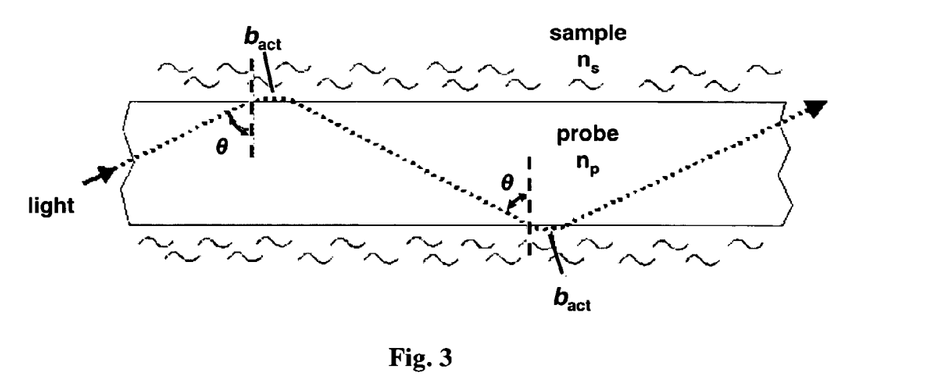
FIG. 3 illustrates the measuring principle of Attenuated Total Reflectance.

FIG. 3 demonstrates the measuring principle of the ATR-probe. In ATR spectroscopy a transparent probe of high refractive index ($n_p$) is brought into contact with a sample which must have a lower refractive index ($n_s$). Light from a spectrometer is lead to the probe via optical fibers and collimated before being introduced into the probe at an angle $\theta$ to the boundary surface. In preferred embodiments of the present invention, $\theta$ is 70° or greater. If the angle of incidence, $\theta$, is greater than the critical angle $\theta_e$ ($\sin \theta_e = n_s/N_p$), total reflection will occur when the beam of light hits the boundary. In each reflection at the boundary between probe material and sample, the light penetrates a short distance into the outer medium (sample) in the form of an evanescent wave. The phenomenon is disclosed in Harrick, J. N., "Internal Reflection Spectroscopy," Wiley, New York 1967 and Schlemmer and Katzer, "ATR Technique For UV/VIS Analytical Measurements," Fresinius Zeit Schrift Für Analytische Chemie, 329, 435-439 (1987), both of which are incorporated herein by reference in their entirety. During this short transection, light can be absorbed by the sample so that the transmitted beam carries information about its spectral properties. The preferred design of the ATR elements results in from one to three reflections of the light before exiting the probe. The light leaves the probe through a lens which focuses it onto a fiber that will bring the light back to the spectrometer for measurement. The optical path length is roughly 1-2 μm per reflection. Therefore, it can be used for measuring very concentrated absorbing species in the solution without diluting the sample.

In addition to the extremely short optical path length, there is a very important and unique feature of the ATR-UV spectrum, which differs from conventional UV spectrum and makes it more powerful than conventional UV technique. The actual or effective pathlength, $b_{act}$, is not a constant parameter for a given ATR flow cell or probe. It is a function of the wavelength, refractive indices $n_s$ and $n_p$, and angle of incidence. Thus, the absorption of a chemical at a fixed concentration, and at a given wavelength can vary differently if other components have an effect on the solution refractive index $n_s$ even though they do not adsorb UV light at that wavelength. Since different chemical compounds contribute to solution refractive index differently, the resulting ATR-UV spectrum, thus, contains a large amount of information about a given solution. This ATR-UV spectrum can provide the individual component concentrations when analyzed by multivariate or linear regression methods. In kraft liquors, it is important to understand that $Na_2OH$ and $Na_2CO_3$ affect the absorption values of $Na_2S$ at 230-250 nm, although they do not themselves absorb in that wavelength range.

First generation AFR probes and flow cells utilized in the prior art could not provide useful UV information at wavelengths below 210 nm. In prior ATR probes, the signal was saturated below 210 nm because the prior ATR elements did themselves strongly absorb light below 210 nm. Because of this limitation, the individual concentrations of two key kraft liquor components, NaOH and $Na_2CO_3$, could not be determined. The prior art was limited to ascertaining the concentrations of components absorbing light with a wavelength greater than 210 nm, e.g. sulfur species. While the prior art could provide an indication of the total concentration of non-absorbing salts like NaOH and $Na_2CO_3$ the inability to determine the individual concentrations of these components significantly limited the prior art systems process control applications.

The inventive system utilizes a second generation ATR probe or flow cell capable of providing useful UV absorbance data at wavelengths as low as 190 nm. This is accomplished through treatment of the ATR probe to prevent UV absorbance by the ATR probe or element below 210 nm. Accordingly, the concentration of chemical components absorbing ultraviolet radiation in the wavelength range of 190-210 nm may now be determined. While the inventive system may be used to measure individual concentrations of any chemical component absorbing in the expanded wavelength range of 190-300 nm, the inventive system is particularly suitable for application to kraft mill process streams where two critical components, NaOH and $Na_2CO_3$, both absorb in the 190-210 nm range and thus, were previously undetectable by prior art systems. Other components for which the present invention may test include but are not limited to KCl, $Na_2SO_4$ and $Na_2SO_3$.

ATR probes and flow cells suitable for use in the claimed invention include all those with the ability to generate analyzable UV absorbance data at wavelengths as low as 190 nm. Preferably ATR probes and flow cells manufactured by Axiom Analytic Inc. (e.g. flow cell models TNL-1201-1V, and FNL-120V, and ATR element model CRE-223-1), are used in this claimed system.

Figure 4:
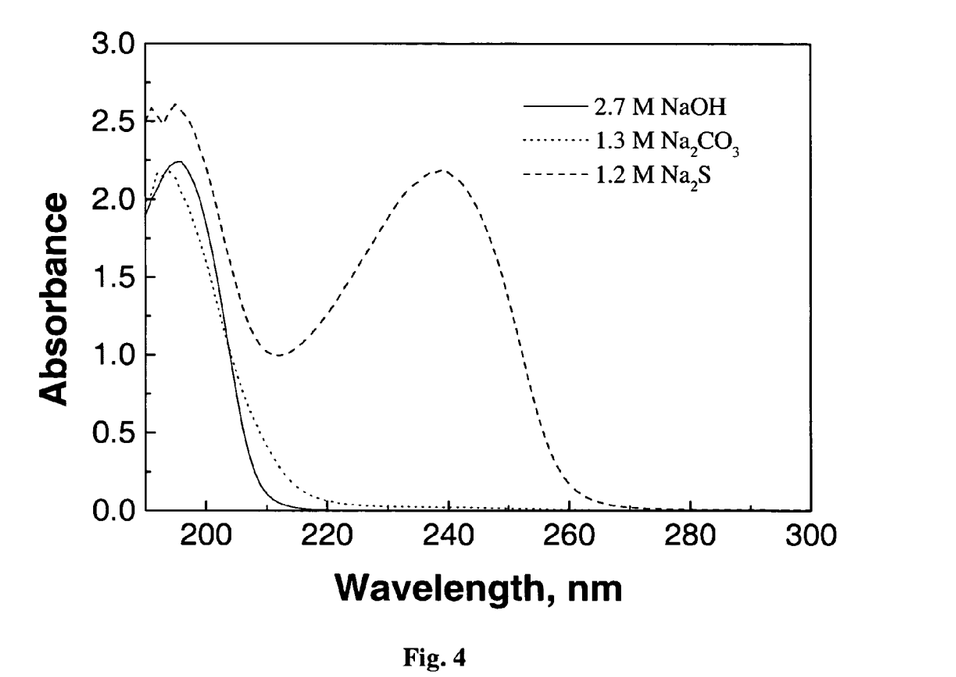
FIG. 4 illustrates three ATR-UV spectra of concentrated solutions of pure sodium hydroxide, sodium carbonate and sodium sulfide.
Figure 5:
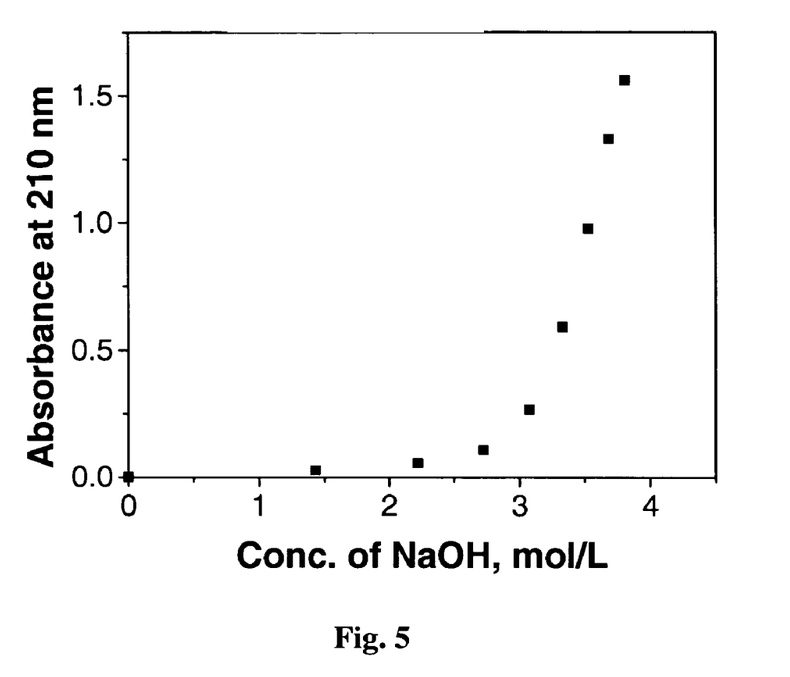
FIGS. 5-7 illustrate that the linear principles of Beer's law is not directly applicable for ATR-UV measurements of sodium hydroxide, sodium carbonate and sodium sulfide, respectively.
Figure 6:
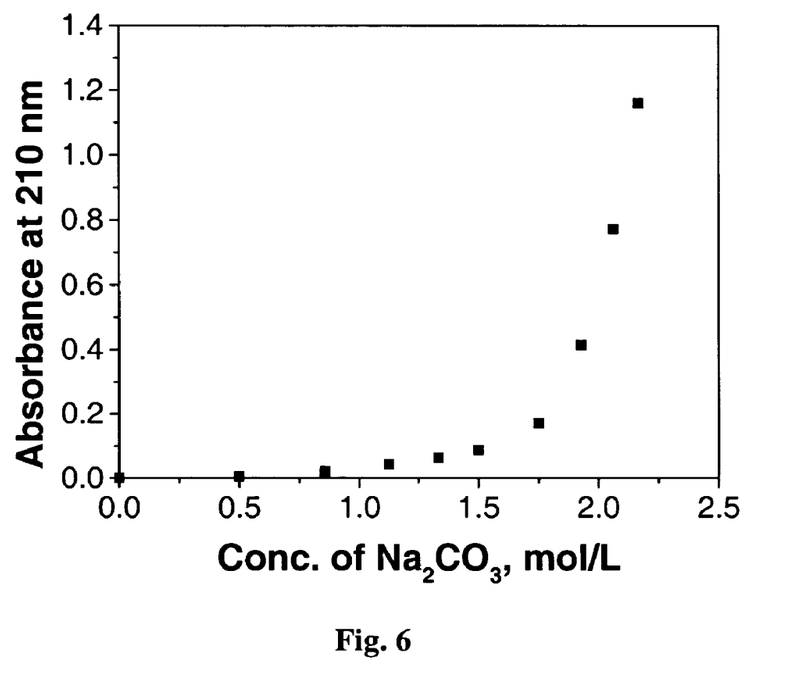
Figure 7:
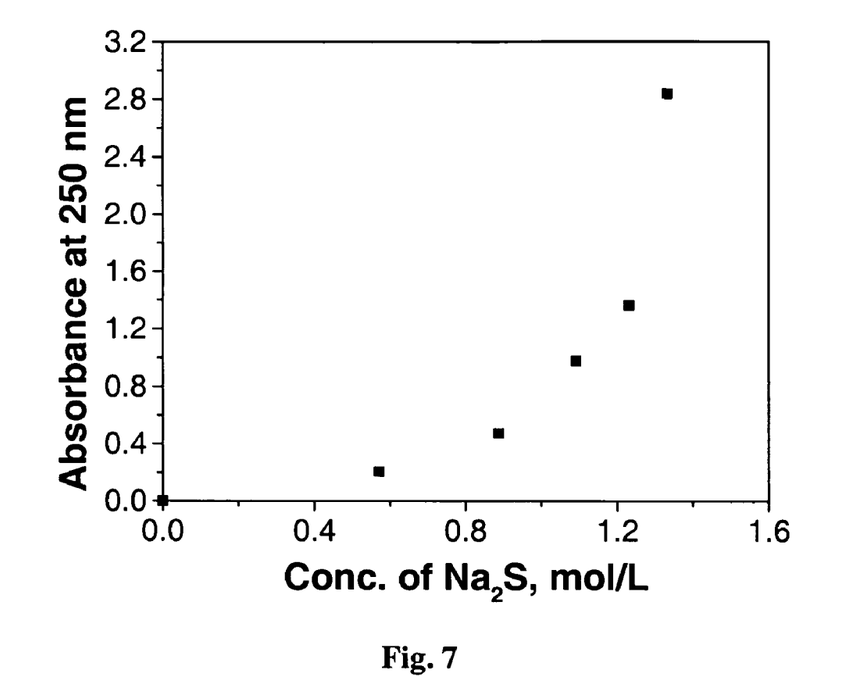

Utilizing an Axiom Analytic ATR flow cell, the inventors discovered that both NaOH and $Na_2CO_3$ absorb ultraviolet light in the wavelength range from 190 to 210 nm, the range previously unanalyzable with first generation ATR cells or conventional UV spectroscopy equipment. FIG. 4 shows the ATR-UV spectra of concentrated solutions for pure sodium hydroxide, pure carbonate and pure sulfide. The sulfide solution shows strong absorbency in the wavelength range of 190 to 260 nm. The previously unknown absorbances of sodium hydroxide and sodium carbonate can be seen at a wavelength around 210 nm. Since NaOH and $Na_2CO_3$ both absorb ultraviolet light in this region, the absorbance data in the 190 to 210 nm range allows simultaneous calculation of the concentrations of both NaOH and $Na_2CO_3$ in addition to the sulfur species previously calculatable by prior art systems. If only one of the two components, NaOH and $Na_2CO_3$, is known to be present in the system, its concentration can be obtained by its effect on the absorbance values of $Na_2S$. When both $Na_2CO_3$ and NaOH are present, their individual concentrations cannot be determined.

Use of multivariate calibration methods for determining component concentrations is well known in the art. See Danielsson et al., Spectroscopic measurements in opaque solutions: UV-Vis spectroscopy on process liquors in the paper and pulp industries, Process Control and Quality 6 (1994) 149-157and U.S. Pat. No. 5,616,214. A multivariate calibration set is built from the ATR-UV spectra of many standard process streams with known and varying chemical concentrations. For example, for kraft mill process control purposes, liquors with known and varying concentrations of sodium hydroxide, sodium sulfide, sodium carbonate, sodium chloride, sodium sulfate and sodium thiosulphate are used to build a calibration set.

Although not necessary, it is generally preferable to account for the concentration of all components contained in the comparative set with a Partial Least Squares (PLS) calibration. The idea of the PLS method of calibration is to reconstruct the spectrum of a mixture by adding fractions of pure component spectra and predict the concentrations of the interested components in the unknown sample.

Once a calibration coefficient matrix is created, the concentrations of the components in an unknown sample can be determined by reconstructing the unknown spectrum from loading vectors in the calibration set. The PLS method minimizes the effects of temperature changes, baseline shifts and component interactions in the sample. Accordingly, the PLS method is preferred for quantitative determination of component concentrations from complicated unknown ATR-UV spectra associated with spectroscopic analysis of complex process streams and pulping liquors, in particular.

Figure 8:
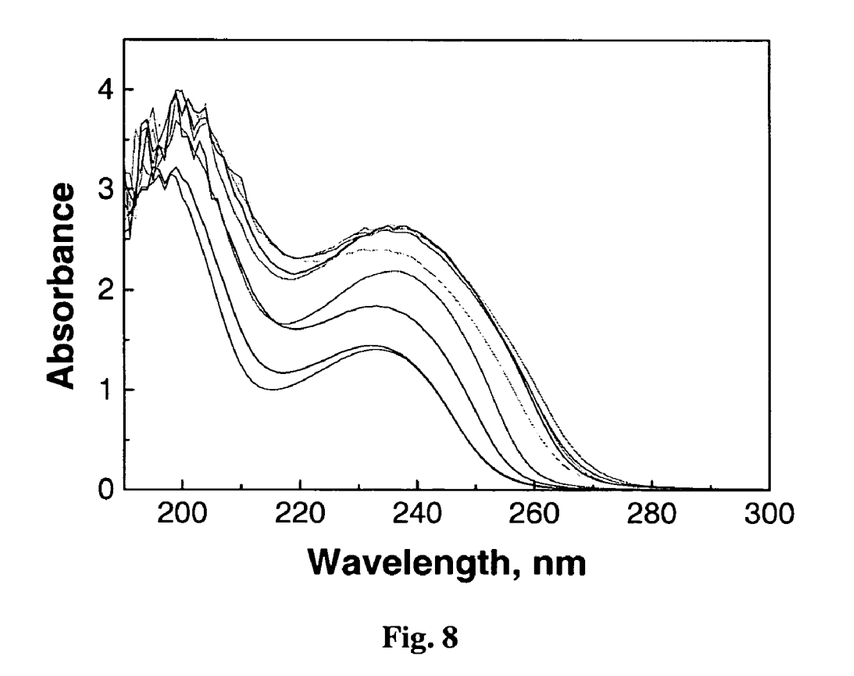
FIG. 8 illustrates ATR-UV spectra for solutions containing varied concentrations of sodium sulfide and sodium carbonate.

Software applications particularly suitable for multivariate calibration include Chemometrical, LabCalc, Math Lab, etc. Using these software programs those skilled in the art can construct calibration files using baseline samples with varying concentrations of key components. For example, varying concentrations of sodium hydroxide, sodium sulfide, sodium carbonate, sodium chloride, sodium sulfate and sodium thiosulphate should be used to construct calibration files for analyzing kraft mill liquor streams. The concentrations of these components should be adjusted to approximate concentrations typically found in the process stream to be monitored. FIG. 8 depicts the ATR-UV spectra of several solutions of effective alkali, sulfide and carbonate as typically found in kraft mill liquor streams. The concentration of each component was changed randomly. The multivariate calibration program analyzes the shift in the ATR-UV spectra of the training samples caused by the varying concentration levels and uses the data to predict the concentration levels of unknown samples.

The present invention allows use of a linear regression method to determine component concentrations if the total concentration of all major components of the process stream does not change significantly. As applied to kraft liquor streams, linear regression may be used if the total salt concentration, i.e. NaOH, $Na_2CO_3$ and $Na_2S$, does not change significantly. Significant fluctuations in total salt concentration affect the refractory index of the liquor resulting in a non-linear relationship between absorbency value and concentration. However, the total salt concentration of most kraft mill processing streams fluctuates only minimally. Accordingly, because the absorbency values from each component are linearly additive at wavelengths below 210 nm the individual component concentrations may be determined through linear regression methods. However, if the processing stream experiences large fluctuations in total salt concentration, the refractory index change of the liquors will make the absorbency value become non-linear, corresponding to the component concentrations and a multivariate regression method must be used for the calibration under such condition. If the fluctuations exceed about 5% then linear regression is not useful. Linear regression is under appropriate circumstances preferred since the calibration is simpler. In addition to simpler calculations, fewer standard solutions are necessary to build the basefile for a linear regression.

By contrast, the prior art only allows for computation of sulfide concentration by linear regression even if there is no large fluctuation in total salt concentration. Further, given the prior art systems inability to distinguish between NaOH and $Na_2CO_3$ concentration levels, it is impossible to determine if their ion concentrations have changed regardless of the regression method, linear or multivariate regression that is used. Thus, prior art systems must utilize a multivariate regression method to eliminate the effect of a possible change in total salt concentration.

Those skilled in the art recognize the importance of controlling NaOH, $Na_2CO_3$ and $Na_2S$ during kraft mill operations. Because the claimed invention quickly provides accurate concentration readings for these key components, it is particularly suitable for controlling operation of a kraft cooking digester, recausticizing unit, white liquor oxidation reactor or chemical recovery furnace.

The system can be applied to any concentrated liquors in which the species of interest absorbs in the UV/Vis region. For example, if NaOH is found lower than the target value while $Na_2CO_3$ is higher in the recausticizing plant, the operator can adjust the amount of CaO dosage to increase the conversion of $Na_2Co_3$ to NaOH. Also, if the low NaOH has reached the digester, the operator can increase the amount of liquor addition to obtain the same rate of digestion.

The following examples are illustrative of, but are not to be construed as limiting, the invention embodied herein.

EXAMPLES

Example 1

Figure 9:
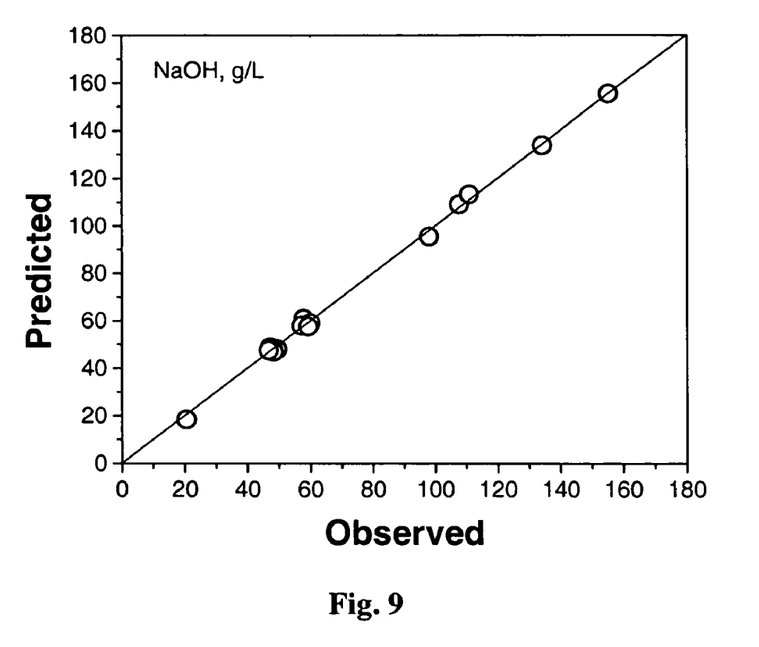
FIGS. 9-11 illustrate the calibration graphs for EA, sulfide and carbonate, respectively.
Figure 10:
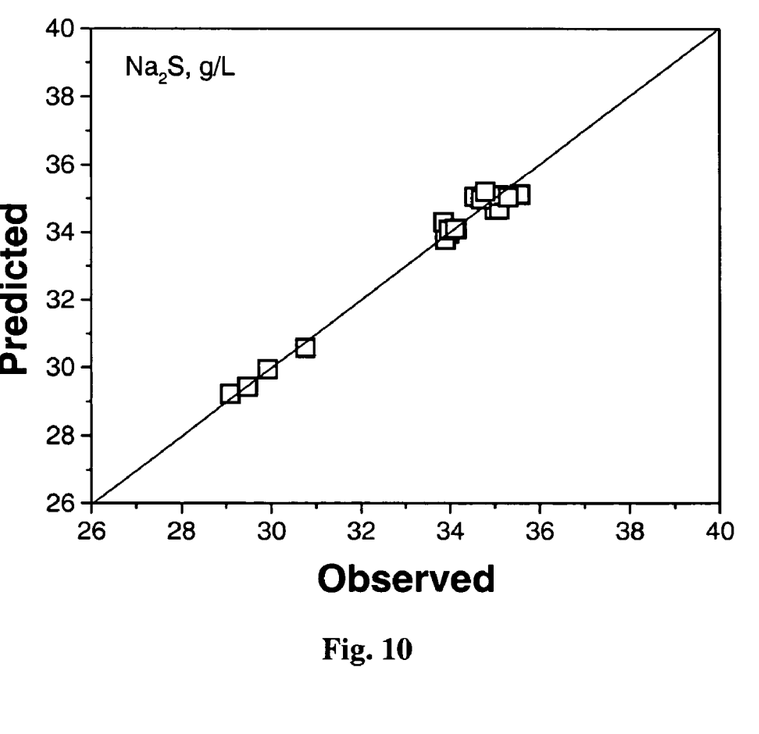
Figure 11:
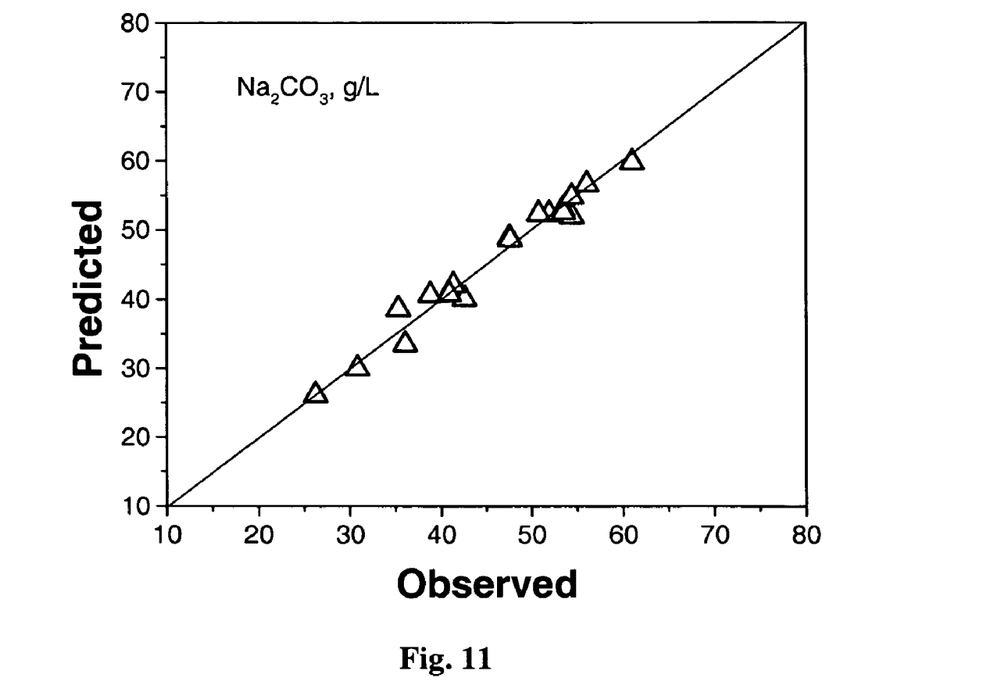
Figure 12:
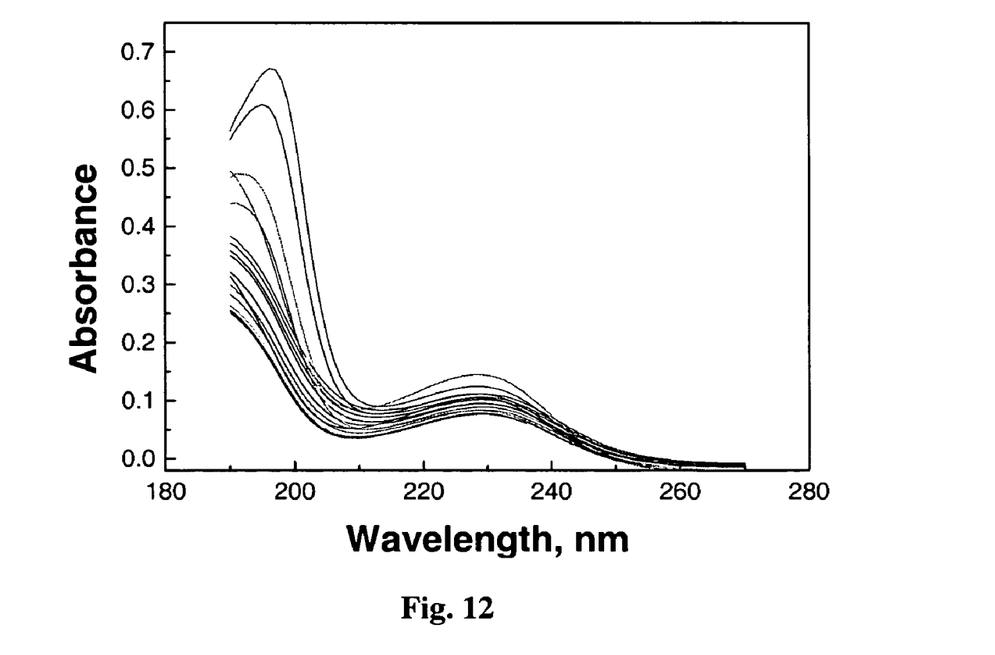

With chemometrical, a multivariate calibration program employing a PLS regression method, a calibration file used for predicting the concentration of typical components in kraft mill liquors was built. A training set of samples, covering the range of concentrations of effective alkali, sulfide and carbonate typically encountered in kraft mill white and green liquors was constructed and analyzed. Table 1 depicts the actual concentrations of the three components for each of the nine training samples used for the calibration model. FIGS. 9, 10, and 11 show the calibration graphs for EA, sulfide and carbonate, respectively. The linear relationships shown indicate the accuracy of the calibration models in predicted concentration. The calibration model accurately predicted the concentrations for EA and sulfide as illustrated by the linear relationships shown in FIG. 9. While the accuracy of the predicted concentration of carbonate suffered at low concentrations, kraft liquors rarely contain such low concentrations of carbonate and, therefore, the practical significance of the deviation at low concentrations is minimal. Since causticizing efficiency normally never gets beyond 90%, the carbonate concentration in all kraft liquors should normally be above 0.3 M. In addition, such error can be further reduced by increasing the number of samples used to build the calibration file.

TABLE 1

Comparison between actual (Obs.) and predicted (by model) data.

| | Effective Alkali, M | | | Sulfide, M | | | Carbonate, M | | |
|---|---|---|---|---|---|---|---|---|---|
| Sample | Obs. | Pred. | Err., % | Obs. | Pred. | Err. % | Obs. | Pred. | Err. % |
| 1 | 2.45 | 2.42 | −1.22 | 0.45 | 0.47 | 4.44 | 0.44 | 0.41 | −6.82 |
| 2 | 2.55 | 2.58 | 1.17 | 0.55 | 0.54 | −1.82 | 0.12 | 0.14 | 16.7 |
| 3 | 2.65 | 2.65 | 0 | 0.65 | 0.65 | 0 | 0.70 | 0.71 | 1.43 |
| 4 | 2.95 | 2.85 | −3.39 | 0.45 | 0.44 | −2.22 | 0.44 | 0.49 | 11.4 |
| 5 | 3.02 | 3.06 | 1.32 | 0.54 | 0.53 | −1.85 | 0.70 | 0.69 | −1.43 |
| 6 | 3.15 | 3.29 | 4.44 | 0.65 | 0.65 | 0 | 0.12 | 0.06 | −1.43 |
| 7 | 3.29 | 3.35 | 1.82 | 0.42 | 0.42 | 0 | 0.65 | 0.64 | −1.54 |
| 8 | 3.51 | 3.55 | 1.14 | 0.53 | 0.54 | 1.89 | 0.42 | 0.39 | −7.14 |
| 9 | 3.75 | 3.57 | −4.80 | 0.65 | 0.65 | 0 | 0.12 | 0.19 | 58.3 |

Example 2

Using the method of Example 1, a training set of samples having a constant sulfide concentration of 0.5 M and varying concentrations of EA and carbonate, was used to build a calibration file. The variation of the EA and carbonate concentrations represents the variations of these concentrations generally found over the entire causticizing process. Table 2 depicts the actual concentrations of the samples compared to the predicted values. The data demonstrates that the inventive system provides an excellent means for determining EA and carbonate concentration during all points of the causticizing process.

TABLE 2

Comparison between actual (Obs.) and predicted (by model) data.

| | Concentration of EA, M | | | Concentration of carbonate, M | | |
|---|---|---|---|---|---|---|
| Sample | Obs. | Pred. | RSD, % | Obs. | Pred. | RSD, % |
| 1 | 0.971 | 0.980 | 0.93 | 1.748 | 1.743 | −0.29 |
| 2 | 1.335 | 1.329 | −0.45 | 1.558 | 1.561 | 0.19 |
| 3* | 1.699 | 1.738 | 2.29 | 1.369 | 1.349 | −1.46 |
| 4 | 2.063 | 2.026 | −1.79 | 1.180 | 1.199 | 1.61 |
| 5 | 2.427 | 2.468 | 1.69 | 0.990 | 0.969 | −2.12 |
| 6 | 2.791 | 2.781 | −0.36 | 0.801 | 0.806 | 0.62 |
| 7* | 3.155 | 3.222 | 2.12 | 0.612 | 0.577 | −5.72 |
| 8 | 3.519 | 3.564 | 1.28 | 0.422 | 0.399 | −5.45 |
| 9 | 3.883 | 3.843 | −1.03 | 0.233 | 0.254 | 9.01 |

Example 3

FIG. 11 shows the spectra of a group of kraft white and green liquors obtained from a paper mill. The spectra were obtained with a one-reflectance ATR prism and were used to build another calibration file. Because the absorption characteristics of each ATR prism is different, it is necessary to prepare multiple standard files. The new calibration file was designed to analyze a set of kraft liquors obtained from a kraft pulp mill. The measured concentrations of NaOH, $Na_2CO_3$ and $Na_2S$ by ABC titration, and predicted by the present method are listed in Table 3. Sample GL is a green liquor, while samples, WL-1, WL-2 and WL-3, are white liquors from different units of the causticizing plant. A strong correlation exists between the actual and predicted concentrations for $Na_2S$ concentration. The error between the actual and predicted concentrations for NaOH and $Na_2CO_3$ is negligible and quite acceptable for kraft mill process control purposes.

While the present invention has generally been described with reference to a kraft liquor stream for papermaking, it would apply equally to other process streams with components having absorbency below 210 nm. The process according to the present invention may also be applicable to liquors used in sulfite pulping processes and bleaching processes. In addition, other embodiments of the invention will be apparent to those skilled in the art from consideration of the specification and practice of the invention disclosed herein. It is intended that the specification and examples be considered as exemplary only, with the true scope and spirit of the invention being indicated by the following claims.

TABLE 3

Chemical concentrations of mill liquors measured by ABC titration and predicted by the present method

| Sample type* | NaOH, g/L | | | Na2S, g/L | | | Na2CO3 | | |
|---|---|---|---|---|---|---|---|---|---|
| | ABC | Pred. | RSD, % | ABC | Pred. | RDS, % | ABC | Pred. | RSD, % |
| GL | 47.2 | 48.9 | 3.8 | 33.9 | 34.3 | 1.3 | 54.4 | 51.9 | −4.7 |
| WL-1 | 107.6 | 109.3 | 1.5 | 29.1 | 29.2 | 0.4 | 36.0 | 33.4 | −7.2 |
| WL-2 | 110.9 | 113.4 | 2.2 | 29.5 | 29.4 | −0.1 | 30.8 | 29.9 | −2.8 |
| WL-3 | 97.9 | 95.6 | −2.4 | 30.8 | 30.6 | −0.6 | 35.3 | 38.6 | 9.3 |

We claimed:

1. A method for simultaneously determining multiple individual chemical concentrations of an undiluted liquid kraft liquor stream comprising:
   providing an undiluted liquid kraft liquor stream;
   subjecting at least a segment of the stream to ultraviolet light wherein the light penetrates a short distance into the segment and the effective path length of the light is a function of the refractive index of the segment;
   generating an ultraviolet absorption spectrum from said ultraviolet penetration of the sample over a wavelength from 190 to 300 nm; and
   analyzing the ultraviolet absorption spectrum by a regression method to determine the multiple component concentrations of the liquid stream;
   wherein the sample is subjected to ultraviolet light by an attenuated total reflectance device configured for preventing ultraviolet absorbance by the device below 210 nm.

2. A method according to claim 1 wherein the attenuated total reflectance device is an ATR-UV optical probe.

3. A method according to claim 1 wherein the attenuated total reflectance device is an ATR-UV tunnel flow cell.

4. A method according to claim 1 wherein the regression method is multivariate.

5. A method according to claim 4 wherein the multivariate regression method is the partial least squares method.

6. A method according to claim 1 wherein the regression method is linear.

7. A method according to claim 1 wherein the measured individual component concentrations of the kraft liquor are selected from sodium hydroxide, sodium sulfide and sodium carbonate.

8. A method according to claim 1 wherein the attenuated total reflectance device comprises an ATR-UV flow cell.

9. A method for simultaneously determining the sodium hydroxide, sodium sulfide and sodium carbonate concentrations of a kraft liquor stream comprising:
   providing a kraft liquor stream;
   generating an ATR-UV absorbency spectrum of the liquor over a wavelength from 190 to 300 nm;
   analyzing the ultraviolet absorption spectrum by a regression method to determine the concentrations of sodium hydroxide, sodium sulfide, and sodium carbonate in the kraft liquor stream.

10. A method according to claim 9 further comprising controlling operation of a kraft cooking digester recausticizing unit, white liquor oxidation reactor or chemical recovery furnace in response to the determined chemical concentrations.

11. A system for simultaneously determining multiple individual chemical concentrations of a liquid kraft liquor stream comprising:
   an undiluted liquid kraft liquor stream source,
   an ultraviolet spectrometer in cooperative relationship with a device in direct communication with the undiluted liquid kraft liquor stream and capable of providing ultraviolet absorption data between 190 and 300 nm from the undiluted liquid kraft liquor stream, and
   a multivariate or linear calibration program for analyzing the provided ultraviolet absorption data, wherein the device is an attenuated total reflectance device configured for preventing ultraviolet absorbance by the device below 210 nm.

12. A system according to claim 11 wherein the attenuated total reflectance device is an ATR-UV optical probe.

13. A system according to claim 11 wherein the attenuated total reflectance device is an ATR-UV tunnel flow cell.

14. A system according to claim 13 wherein the ATR-UV tunnel flow cell is installed in the ultraviolet spectrometer and a liquid kraft liquor stream flows through the ATR tunnel flow cell.

15. The system according to claim 14, wherein the ATR-UV tunnel flow cell comprises a pump and the kraft liquor stream is pumped through the ATR-UV tunnel flow cell.

16. The system according to claim 14, further comprising a light source which directs light through the ATR-UV tunnel flow cell to the ultraviolet spectrometer.

17. A system according to claim 11 wherein the attenuated total reflectance device comprises an ATR-UV flow cell.

18. The system according to claim 17 wherein the ATR-UV flow cell is installed in the ultraviolet spectrometer and a liquid kraft liquor stream flows through the ATR flow cell.

19. The system according to claim 18, further comprising a pump and the kraft liquor stream is pumped through the ATR-UV flow cell.

20. The system according to claim 18, further comprising a light source which directs light through the ATR-UV tunnel flow cell to the ultraviolet spectrometer.

21. A system for determining chemical concentrations of NaOH and $Na_2CO_3$ in a kraft liquor stream comprising:
   an ultraviolet spectrometer,
   an attenuated total reflectance device capable of providing ultraviolet absorption data between 190 and 300 nm and configured for preventing ultraviolet absorbance by the device below 210 nm, wherein the attenuated total reflectance device transmits the ultraviolet absorption data to the ultraviolet spectrometer by fiber optic cable, and
   a multivariate or linear calibration program for analyzing the ultraviolet absorption data.

22. A system according to claim 21 wherein the attenuated total reflectance device is an ATR-UV optical probe installed in a kraft liquor stream.

23. A system according to claim 21 wherein the attenuated total reflectance device is an ATR-UV tunnel flow cell installed in the ultraviolet spectrometer and a kraft liquor stream flows through the ATR-UV tunnel flow cell.

24. The system according to claim 23, wherein the ATR-UV tunnel flow cell comprises a pump and the kraft liquor stream is pumped through the ATR-UV tunnel flow cell.

25. The system according to claim 23, further comprising a light source which directs light through the ATR-UV tunnel flow cell to the ultraviolet spectrometer.

26. The system according to claim 21 wherein the attenuated total reflectance device comprises an ATR-UV flow cell installed in the ultraviolet spectrometer and a kraft liquor stream flows through the ATR flow cell.

27. The system according to claim 26, wherein the ATR-UV flow cell comprises a pump and the kraft liquor stream is pumped through the ATR-UV flow cell.

28. The system according to claim 26, further comprising a light source which directs light through the ATR-UV flow cell to the ultraviolet spectrometer.

* * * * *